(12) United States Patent
Gliner et al.

(10) Patent No.: US 11,517,218 B2
(45) Date of Patent: Dec. 6, 2022

(54) SELECTIVE GRAPHICAL PRESENTATION OF ELECTROPHYSIOLOGICAL PARAMETERS

(71) Applicant: Biosense Webster (Israel) Ltd., Yokneam (IL)

(72) Inventors: Vadim Gliner, Haifa (IL); Alexander Salevich, Haifa (IL); Yair Palti, Herzelia (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 100 days.

(21) Appl. No.: 16/723,592

(22) Filed: Dec. 20, 2019

(65) Prior Publication Data
US 2021/0186363 A1    Jun. 24, 2021

(51) Int. Cl.
*A61B 5/00*       (2006.01)
*A61B 5/06*       (2006.01)
*A61B 34/20*      (2016.01)
*A61B 5/339*      (2021.01)
*A61B 5/287*      (2021.01)
*G06T 19/00*      (2011.01)

(52) U.S. Cl.
CPC .............. *A61B 5/062* (2013.01); *A61B 5/287* (2021.01); *A61B 5/339* (2021.01); *A61B 34/20* (2016.02); *G06T 19/003* (2013.01)

(58) Field of Classification Search
CPC combination set(s) only.
See application file for complete search history.

(56) References Cited

U.S. PATENT DOCUMENTS

| | | |
|---|---|---|
| 5,391,199 A | 2/1995 | Ben-Haim |
| 6,236,883 B1 | 5/2001 | Ciaccio et al. |
| 6,239,724 B1 | 5/2001 | Doron et al. |
| 6,332,089 B1 | 12/2001 | Acker et al. |

(Continued)

FOREIGN PATENT DOCUMENTS

| | | |
|---|---|---|
| WO | WO 96/05768 A1 | 2/1996 |
| WO | WO 2020/185339 A1 | 9/2020 |

OTHER PUBLICATIONS

Extended European Search Report dated May 17, 2021. for Application No. 20215542.0, 8 pages.

*Primary Examiner* — Joel F Brutus
(74) *Attorney, Agent, or Firm* — Frost Brown Todd LLC

(57) ABSTRACT

A medical apparatus includes a probe configured for insertion into a body of a patient. The probe includes electrodes configured to contact tissue within the body. The apparatus further includes a display screen, a position-tracking system configured to acquire position coordinates of the electrodes, and a processor. The processor is configured to acquire electrophysiological signals from a group of the electrodes in a sequence of time intervals, extract electrophysiological parameters from the signals, and for each time interval, compute a measure of consistency of the parameters extracted from the signals. The processor is further configured to render to the display screen a three-dimensional map of the tissue while superimposing on the map a visual indication of the extracted parameters for which the measure of consistency satisfied a consistency criterion, and automatically discarding from the map the parameters for which the measure of consistency did not satisfy the criterion.

20 Claims, 3 Drawing Sheets

(56) References Cited

U.S. PATENT DOCUMENTS

| | | |
|---|---|---|
| 6,484,118 B1 | 11/2002 | Govari |
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2012/0101398 A1 | 4/2012 | Ramanathan et al. |
| 2013/0006131 A1 | 1/2013 | Narayan et al. |
| 2015/0057507 A1 | 2/2015 | Koyrakh et al. |
| 2016/0045123 A1* | 2/2016 | Bar-Tal .................. A61B 5/349 600/515 |
| 2016/0100770 A1 | 4/2016 | Afonso et al. |
| 2018/0042505 A1* | 2/2018 | Botzer .................. A61B 5/287 |

* cited by examiner

SELECTIVE GRAPHICAL PRESENTATION OF ELECTROPHYSIOLOGICAL PARAMETERS

FIELD OF THE INVENTION

The present invention relates generally to electrophysiological measurements, and particularly to apparatus and methods for automated mapping of electrophysiological parameters.

BACKGROUND

An electrophysiological (EP) map of a tissue of a patient is generated by positioning one or more electrodes on a region of the tissue, acquiring an EP signal of the region, and then repeating the process for a different region. EP parameters are extracted from the EP signals in each region of measurement, and then displayed over an image of the tissue.

SUMMARY

Embodiments of the present invention that are described hereinbelow provide improved methods and apparatus for mapping of electrophysiological parameters.

There is therefore provided, in accordance with an embodiment of the present invention, a medical apparatus, which includes a probe configured for insertion into a body of a patient. The probe includes a plurality of electrodes configured to contact tissue within the body in a sequence of time intervals. The apparatus further includes a display screen, a position-tracking system configured to acquire position coordinates of the electrodes within the body, and a processor.

The processor is configured to acquire respective electrophysiological signals from a group of the electrodes in each time interval in the sequence while the electrodes contact an area of the tissue at respective locations within the area, to extract respective electrophysiological parameters from the respective electrophysiological signals acquired in each time interval by the electrodes in the group, and, for each time interval, to compute a respective measure of consistency among the respective electrophysiological parameters extracted from the electrophysiological signals acquired by the electrodes in the group during the time interval. The processor is further configured to render to the display screen a three-dimensional (3D) map of the tissue while superimposing on the map, responsively to the position coordinates, a visual indication of the extracted electrophysiological parameters at the respective locations of the electrodes in the time intervals for which the respective measure of consistency satisfied a predefined consistency criterion, and to discard automatically from the map the electrophysiological parameters extracted in the time intervals for which the respective measure of consistency did not satisfy the predefined consistency criterion.

In some embodiments, the electrophysiological parameter includes a local activation time (LAT) in a heart of the patient, and the measure of consistency is indicative of a variation of the LAT. In one embodiment, the measure of consistency includes a peak-to-peak variation of the LAT in any given time interval, and the consistency criterion requires that the peak-to-peak variation of the LAT not exceed a predefined limit.

Alternatively or additionally, the electrophysiological parameter includes an electrophysiological voltage, and the measure of consistency is indicative of a variation of the electrophysiological voltage. In one embodiment, the measure of consistency includes a peak-to-peak variation of the electrophysiological voltage in any given time interval, and the consistency criterion requires that the peak-to-peak variation of the electrophysiological voltage not exceed a predefined limit.

In yet another embodiment, the 3D map is rendered in a background color, and the visual indication includes other colors superimposed on the background color at the respective locations to indicate a value of the extracted electrophysiological parameter.

There is also provided, in accordance with an embodiment of the present invention, a method for electrophysiological mapping. The method includes acquiring in a sequence of time intervals respective electrophysiological signals from a group of electrodes on a probe while the electrodes contact an area of tissue within a body of a patient, and acquiring position coordinates of the group of electrodes. Respective electrophysiological parameters are extracted from the respective electrophysiological signals acquired in each time interval in the sequence by the electrodes in the group, and a respective measure of consistency is computed for each time interval among the respective electrophysiological parameters extracted from the electrophysiological signals acquired by the electrodes in the group during the time interval. The method further includes displaying a three-dimensional (3D) map of the tissue while superimposing on the map, responsively to the position coordinates, a visual indication of the extracted electrophysiological parameters at the respective locations in the time intervals for which the respective measure of consistency satisfied a predefined consistency criterion, and automatically discarding from the map the electrophysiological parameters extracted in the time intervals for which the respective measure of consistency did not satisfy the predefined consistency criterion.

The present invention will be more fully understood from the following detailed description of the embodiments thereof, taken together with the drawings in which:

DETAILED DESCRIPTION OF EMBODIMENTS

Overview

Figure 1:
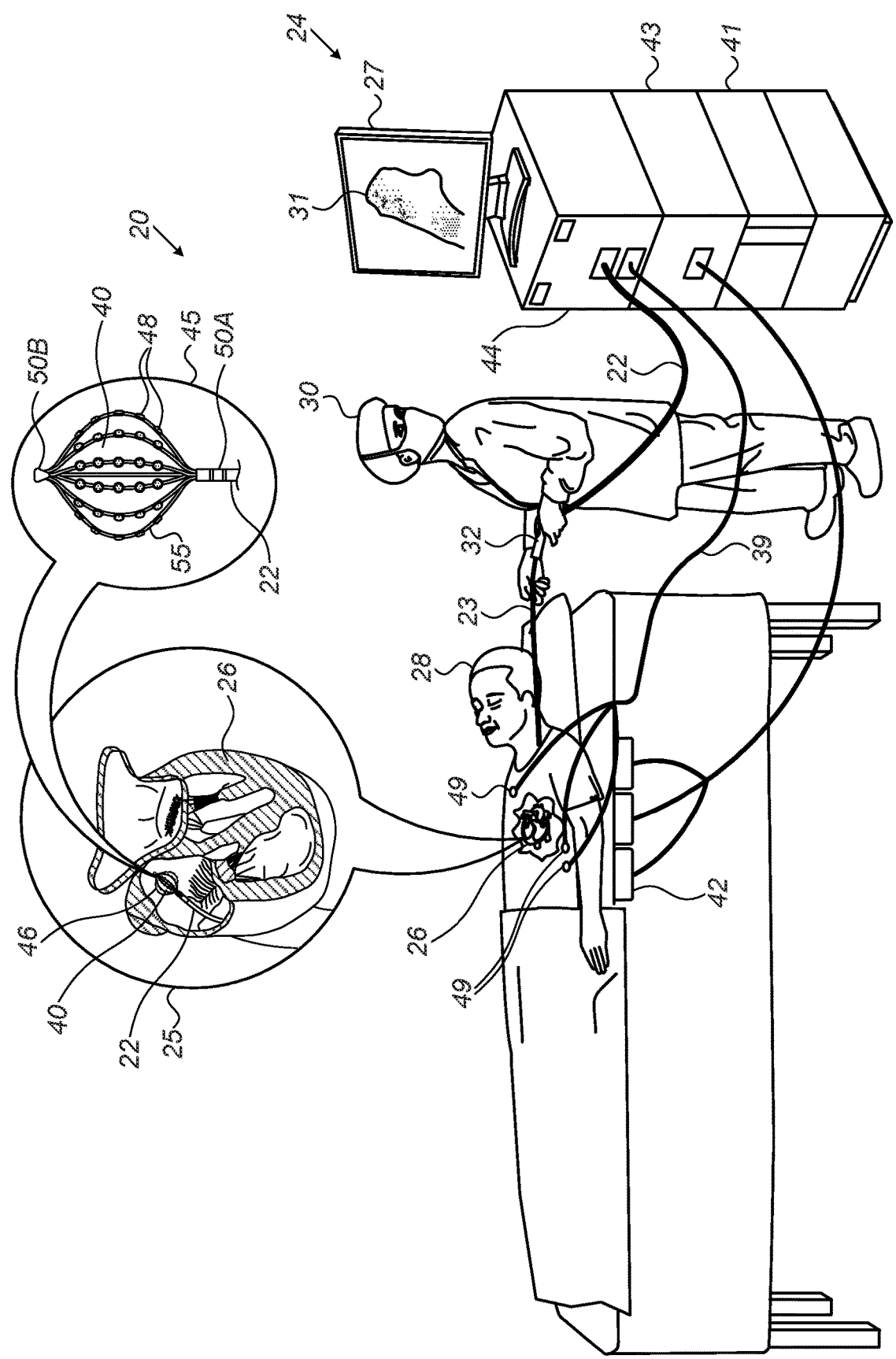
FIG. 1 is a schematic pictorial illustration of a medical apparatus for mapping an EP parameter in a heart of a patient, in accordance with an embodiment of the present invention.

Generating an electrophysiological (EP) map of a tissue of a patient involves positioning one or more electrodes on a region of the tissue, acquiring the signal of the region, and then repeating the process for a different region. When small numbers of electrodes are used, this process generates accurate maps of the EP parameters extracted from these signals, since the physician can observe the acquired signals, and only accept "good" signals (as judged by the physician) into the map. A good signal is typically generated only when the electrode is in good contact with the tissue. Using a small number of electrodes has, however, the drawback that the mapping takes a long time.

For catheters with large numbers of electrodes, the mapping time is reduced, but the accuracy is decreased, since the physician is incapable of properly inspecting all the simultaneously generated signals within the available time. The task of accepting good signals (and rejecting others) may be facilitated by presenting to the physician the analyzed results of the signals, i.e., the values of an EP parameter across the measured region. (For the sake of brevity, "value of an EP parameter" will in the following description be referred to simply as "EP parameter.") The task may be further facilitated by presenting these values in a graphical form, such as a map of the values. However, the physician is still required to use his/her subjective judgement in accepting or rejecting the analyzed results, with an inherent variability in the acceptance due to subjectivity. Moreover, requiring the physician to judge the quality of these results will further tax his/her time and attention during the mapping procedure, especially if a large number of electrodes is used.

The embodiments of the present invention that are described herein address these problems by providing a medical apparatus comprising a probe, a display screen, a position-tracking system, and a processor. The probe, which comprises multiple electrodes, is inserted into the body of a patient so that a group of the electrodes contacts an area of tissue within the body. The group of electrodes can include all the electrodes on the probe or a certain subset of the electrodes. (For example, the group may include 20 electrodes that contact a certain area of myocardial tissue, typically an area on the order of 1-10 $cm^2$, out of a total of 120 electrodes on a basket catheter.) While the electrodes contact the tissue, the processor acquires EP signals from the electrodes in a sequence of time intervals, such as a sequence of heartbeats. Simultaneously, the position-tracking system acquires the position coordinates of the electrodes.

For each time interval, the processor extracts the respective EP parameters from the signals, and computes a measure of consistency of the values of the EP parameters across the electrodes in the group. For brevity, the EP parameters extracted at a given time interval from the group of electrodes contacting an area of the tissue will be referred to as a "set of EP parameters." The processor renders to the display screen a three-dimensional (3D) map of the tissue while superimposing on the map a visual indication, such as colors representing the parameter values, of the set of EP parameters for the points in time for which the measure of consistency satisfied a predefined consistency criterion. The processor automatically discards from the map the EP parameters for which the respective measure of consistency did not satisfy the predefined criterion.

This approach facilitates an automatic presentation of a map of valid EP parameters, without having to rely on a subjective and time-consuming assessment of the EP signals or parameters by the physician.

In a disclosed embodiment, the processor displays a 3D map of a chamber of the heart in which EP parameter is being mapped. The 3D map is presented in a neutral tone, such as gray. The EP parameter may comprise, for example, a local activation time (LAT) measured in the myocardium or a bipolar or unipolar maximum voltage. LAT is the time interval between a reference time determined, for example, from the body surface ECG or intracardiac electrogram, and the time of the local depolarization event. Other useful scalar functions of the physiological parameters may be calculated and displayed, superimposed on a combined display of LAT (as pseudocolor) and/or propagation velocity (as arrows). One such useful scalar function is the range of voltages measured at each sampled point (displayed as a pseudocolor): An abnormally low range is diagnostic of scar tissue, upon which the conduction velocity may be displayed as arrows. LAT can be determined manually or automatically, for example, by marking one or more of (a) the maximum negative slope of the voltage of the unipolar recording (−dV/dt); (b) the maximum absolute voltage of the bipolar recording; (c) the maximum absolute slope dV/dt of the bipolar recording; or (d) the minimum voltage of the bipolar recording. (Methods for automated computation of the LAT are known in the art, for example as implemented in the CARTO® system, produced by Biosense Webster Inc., Irvine, Calif.)

During the measurement process in the heart, the processor extracts a set of EP parameters in each of several (for example 3-7) heartbeats from all of the electrodes contacting the tissue. (Alternatively, time intervals for the measurements may be independent of the heartbeats.) As the area where the electrodes contact the tissue is small by comparison with the chamber of the heart, the EP parameters within a set are expected to vary from each other by only a small amount. Therefore, a large variability between the EP parameters of a set is an indication of improper acquisition of the EP signals. A reason for improper EP signal acquisition may be, for example, poor contact between one or more electrodes and the tissue. In order to identify and reject improperly-acquired EP signals, the processor computes a measure of consistency within each set of EP parameters. The measure of consistency may be, for example, a peak-to-peak variation within the set of EP parameters across the group of electrodes.

The processor rejects sets of EP parameters for which the measure of consistency does not satisfy a predefined consistency criterion, whereas it accepts EP parameters that satisfy the consistency criterion. The processor updates the 3D map by superimposing onto the map an overlay, indicating the values of the accepted sets of EP parameters. The indication may be, for example, a color code, wherein the lowest value of the EP parameter is denoted by blue, the highest by red, and the intermediate values by the colors of the visible spectrum between blue and red. When several sets of EP parameters are accepted in a given area, the processor may overlay the 3D map with, for example, an average of the accepted sets. Alternatively, the processor may overlay the accepted sets onto the map one after the other, or overlay it with only one of the accepted sets.

System Description

FIG. 1 is a schematic pictorial illustration of a medical apparatus 20 for mapping an EP parameter in a heart 26 of a patient 28, in accordance with an embodiment of the present invention.

A physician 30 navigates a basket catheter 40, seen in detail in an inset 45, to a target location in heart 26 of patient 28, by manipulating a shaft 22, using a manipulator 32 near the proximal end of the catheter, and/or deflection from a sheath 23. In the embodiment seen in an inset 25, physician 30 uses catheter 40 to perform electro-anatomical mapping of a cardiac chamber. EP signals are acquired from tissue by using a group of electrodes 48 on basket catheter 40 touching the tissue in an area 46, as further detailed below. When a basket catheter is used, the group of electrodes is in general a smaller subset of the total number of electrodes 48, for example, 20 out of a total of 120 electrodes.

Catheter 40 is inserted in a collapsed configuration, through sheath 23, and only after the catheter exits sheath 23 does the catheter expand to its intended functional shape, as shown in inset 45. By containing catheter 40 in a collapsed configuration, sheath 23 also serves to minimize vascular trauma on its way to the target location.

Basket catheter 40 incorporates a magnetic sensor 50A, seen in inset 45, at the distal edge of shaft 22 (i.e., at the proximal edge of basket catheter 40). Typically, although not necessarily, sensor 50A is a Triple-Axis Sensor (TAS), comprising three miniature coils oriented in different directions. In the pictured embodiment, a second magnetic sensor 50B is incorporated in a distal edge of the basket catheter. Sensor 50B may be a Single-Axis Sensor (SAS) or a Triple-Axis Sensor (TAS), for example. Alternatively, catheter 40 may comprise other sorts of magnetic sensors, at these or other locations.

Catheter 40 further comprises multiple expandable spines 55, which may be mechanically flexible, to each of which are coupled multiple electrodes 48 for a total of, for example, 120 electrodes. Electrodes 48 are configured to touch the tissue of patient 28 for sensing EP signals. Magnetic sensors 50A and 50B and electrodes 48 are connected by wires running through shaft 22 to various processing circuits in a console 24.

Alternatively, apparatus 20 may comprise other types of catheters, with other sorts of electrode arrays, such as an inflatable balloon catheter with electrodes 48 on its outer surface.

Medical apparatus 20 comprises a magnetic-sensing subsystem for determining the position and orientation of basket catheter 40, and thereby the positions of electrodes 48. Patient 28 is placed in a magnetic field generated by a pad containing magnetic field generator coils 42, which are driven by a tracking module 43 in console 24. The magnetic fields generated by coils 42 give rise to electrical signals in sensors 50A and 50B, which are indicative of the position and/or orientation of the sensors. The signals form sensors 50A and 50B are transmitted back to tracking module 43, which converts the signals to corresponding digital inputs to a processor 41. Processor 41 uses these inputs to calculate the position and orientation of basket catheter 40 and thus to find the respective location of each of electrodes 48.

Methods of position and/or orientation sensing using external magnetic fields and magnetic sensors, such as sensors 50A and 50B, are implemented in various medical applications, for example, in the CARTO® system, available from Biosense Webster, Inc. (Irvine, Calif.). Such methods are described in detail in U.S. Pat. Nos. 5,391,199, 6,690, 963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1, issued as U.S. Pat. No. 7,729,742 on Jun. 1, 2010; and 2004/0068178 A1, now abandoned whose disclosures are all incorporated herein by reference with a copy provided in the Appendix.

Alternatively or additionally, apparatus 20 may use other methods of position sensing to find the locations of electrodes 48. For example, processor 41 may map the locations of electrodes 48 by measuring impedances between electrodes 48 and body-surface electrodes 49, which are placed on the chest of patient 28 and connected to console 24 by leads 39.

Processor 41 additionally receives electrophysiological signals via electrical interface 44, and uses the information contained in these signals together with the coordinates provided by magnetic sensors 50A and 50B to construct an electro-anatomical map 31 of the chamber of heart 26 in which catheter 40 is located. During and/or following the procedure, processor 41 may render electro-anatomical map 31 to a display screen 27 (detailed further in FIG. 3.)

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables the processor to perform the disclosed steps, as described below.

The example illustration shown in FIG. 1 is chosen purely for the sake of conceptual clarity. FIG. 1 shows only elements related to the disclosed techniques for the sake of simplicity and clarity. Medical apparatus 20 typically comprises additional modules and elements that are not directly related to the disclosed techniques, and thus are intentionally omitted from FIG. 1 and from the corresponding description. The elements of medical apparatus 20 and the methods described herein may be further applied, for example, to control an ablation of tissue of heart 26.

Measurement and Display of EP Parameters

Figure 2:
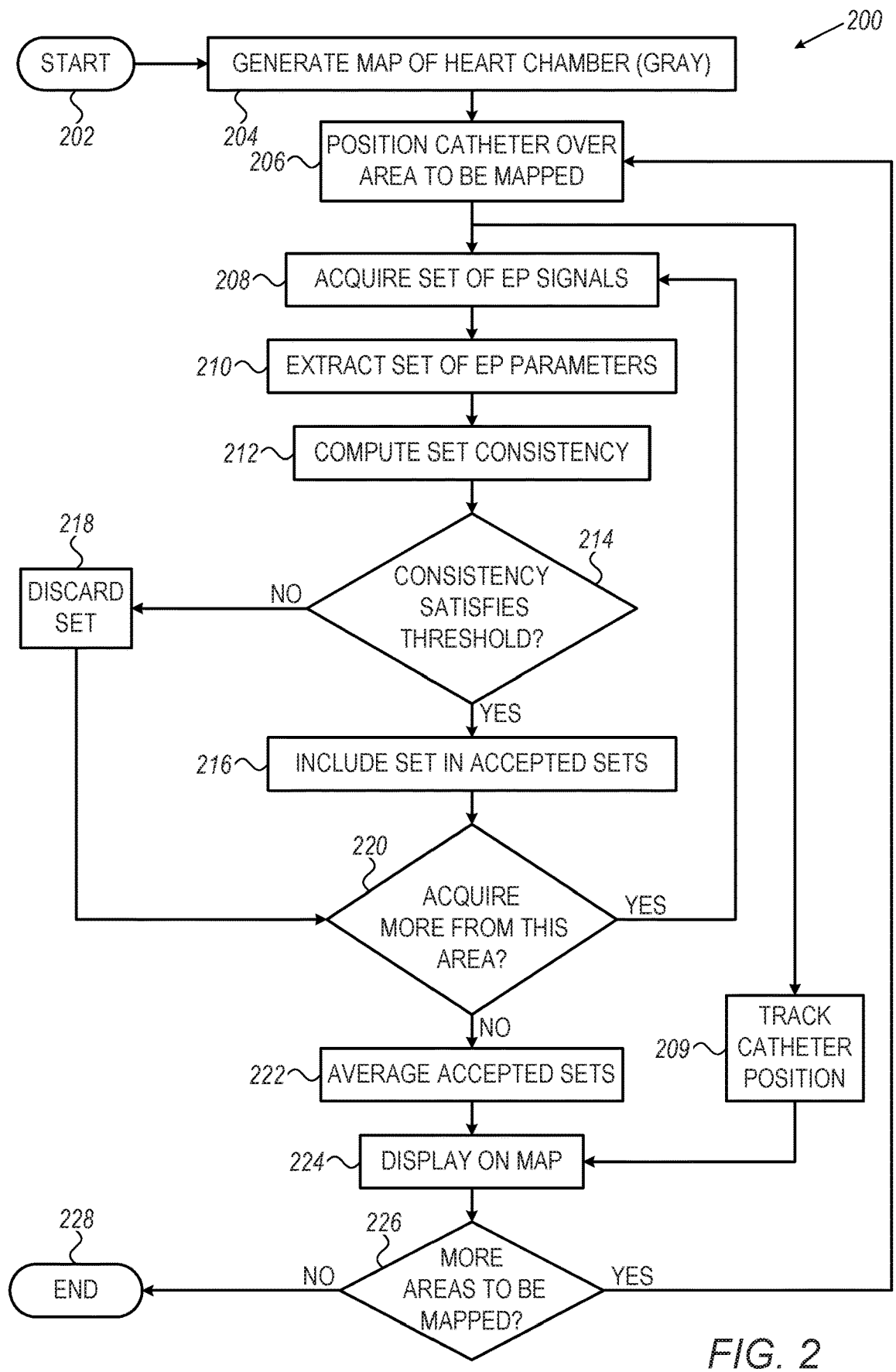
FIG. 2 is a flowchart that schematically illustrates a method for automated EP mapping, in accordance with an embodiment of the invention.

FIG. 2 is a flowchart 200 that schematically illustrates an automated process for EP mapping, in accordance with an embodiment of the invention. In this method, EP parameters from area 46 are incorporated in the map only when they satisfy a certain consistency criterion. The embodiment shown in flowchart 200 refers to an example of acquiring EP signals from a chamber of heart 26 (with reference to FIG. 1). In alternative embodiments, the values of EP parameters may be acquired using other sorts of mapping apparatus, not only from the heart, but also from other organs and tissue, as will be apparent to those skilled in the art after reading the present description.

The process illustrated by flowchart 200 begins in a start step 202. In a map generation step 204, a uniformly gray (or other suitable background color) 3D map of the heart chamber is generated by processor 41 and rendered onto display screen 27. The 3D map is generated, for example, from an image of heart 26 previously stored in the processor, or based on position measurements taken by a catheter. Alternatively, the 3D map may be generated concurrently with displaying the EP parameters. In a catheter positioning step 206, physician 30 positions catheter 40 in heart 26 so that a group of electrodes 48 are in contact with myocardial tissue in area 46 of a chamber of the heart. In an acquisition step 208, processor 41 receives, during a single time interval (such as a single heartbeat) signals from the group of electrodes 48. In a tracking step 209, processor 41 receives signals from tracking module 43, and computes the respective location coordinates of electrodes 48. In an extraction step 210, processor 41 extracts the set of EP parameters from the signals received in acquisition step 208.

In a consistency computation step 212, processor 41 computes the measure of consistency for the set of EP parameters extracted in extraction step 210. The measure of consistency, as well as the consistency criterion, are defined in the present embodiment in terms of the peak-to-peak variation of the EP parameters across a given set. For example, when the EP parameter computed in step 210 is the local activation time (LAT), the consistency criterion can be taken as a range of ±10 ms, i.e., if the LATs within the set are within 20 ms of each other, they are considered to satisfy the consistency criterion. In another example, when the EP parameter is a bipolar or unipolar maximum voltage in the signals sensed by electrodes 48, the consistency criterion can be taken as a range of 20 mV, so that measured maximum voltages within this range are considered to satisfy the consistency criterion. Alternatively, larger or smaller ranges of the parameters can be taken as the consistency criterion.

Further alternatively, other sorts of consistency criteria can be applied. For example, processor 41 may compute the mean value of the EP parameter in question and the variance of the parameter over the sequence of heartbeats, and may define the consistency criterion in terms of the maximal acceptable variance.

In a first decision step 214, processor 41 compares the measure of consistency computed in step 212 to the predefined consistency criterion. If the measure of consistency satisfies the consistency criterion, processor 41 includes the set of EP parameters in the accepted sets, in an inclusion step 216. If the measure of consistency does not satisfy the criterion, processor 41 discards the set of EP parameters, in a discard step 218.

Both from inclusion step 216 and discard step 218, the process continues to a second decision step 220, where processor 41 determines, based on a preset criterion, whether more sets of EP parameters are to be acquired from the current area 46. Additional acquisitions may be required, if, for example, the measure of consistency did not satisfy the consistency criterion for any of the sets of EP parameters acquired from the current area 46. Alternatively or additionally, further acquisitions may be desirable in order to average over a large number of accepted sets. When more acquisitions are required, the process returns to step 208.

When no more acquisitions are required, the sets of EP parameters collected in step 216 may optionally be averaged in an averaging step 222. Alternatively, averaging step 222 may be bypassed, and only one of the accepted sets of EP parameters may be chosen for output. A representation of the resulting EP parameters (averaged or not) is superimposed on the 3D map in a display step 224. In a display step 224, processor 41 displays the EP parameters, for example by applying a corresponding color code to the appropriate region of the 3D map generated in step 204, based on the position coordinates received in tracking step 209. The color-coding may comprise, for example, showing the lowest values of the EP parameter as a blue color, the highest values as a red color, and intermediate values between the lowest and highest values in the same order as colors in a visible spectrum. However, other color-coding schemes, as well as other sorts of shading or symbols, such as are known in the art, may alternatively be used.

After display step 224, the process continues to a third decision step 226, where physician 30 decides whether additional areas will be included in the mapping. When the decision is affirmative, physician 30 moves catheter 40 into a new area 46 in step 206, and the process continues from there as described above. When physician 30 decides that the mapping has been completed, the process ends in an end step 228.

Figure 3:
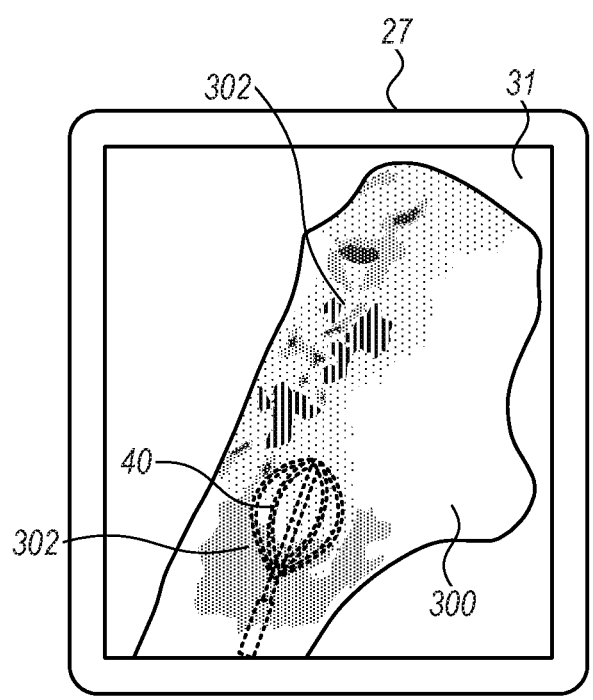
FIG. 3 is a schematic illustration of an electro-anatomical map, in accordance with an embodiment of the invention.

FIG. 3 is a schematic illustration of electro-anatomical map 31, in accordance with an embodiment of the invention. A 3D map 300 is initially colored in a neutral color, such as gray, on display screen 27, following step 204 (FIG. 2).

When the EP parameters acquired by basket catheter 40 satisfy the applicable consistency criterion, a colored overlay 302 is superimposed on 3D map 300 in accordance with the method of FIG. 2.

Although the embodiment described above relates to measurement of EP parameters in heart 26, in alternative embodiments the described method of automated acceptance or rejection of EP parameters may be applied to other tissues of the body of patient 28. Moreover, in alternative embodiments more than one type of EP parameter may be measured and displayed simultaneously.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
    a probe configured for insertion into a body of a patient and comprising a plurality of electrodes configured to contact tissue within the body in a sequence of time intervals;
    a display screen;
    a position-tracking system configured to acquire position coordinates of the electrodes within the body; and
    a processor configured to:
        acquire a respective electrophysiological signal from a group of the electrodes in each time interval in the sequence while the electrodes contact an area of the tissue at respective locations within the area;
        extract respective electrophysiological parameters from the respective electrophysiological signals acquired in each time interval by the electrodes in the group;
        for each time interval, compute a respective measure of consistency among the respective electrophysiological parameters extracted from the electrophysiological signals acquired by the electrodes in the group during the time interval, the respective measure of consistency comprising a variation range; and
        render to the display screen a three-dimensional (3D) map of the tissue while superimposing on the map, responsively to the position coordinates, a visual indication of the extracted electrophysiological parameters at the respective locations of the electrodes in the time intervals for which the variation range of the respective measure of consistency is smaller than a predefined range of a predefined consistency criterion, and automatically discarding from the map the electrophysiological parameters extracted in the time intervals for which the variation range of the respective measure of consistency is larger than the predefined range of the predefined consistency criterion.

2. The medical apparatus according to claim 1, the electrophysiological parameter comprising a local activation time (LAT) in a heart of the patient, and the measure of consistency is indicative of a variation of the local activation time (LAT).

3. The medical apparatus according to claim 2, the measure of consistency comprising a peak-to-peak variation of the local activation time (LAT) in any given time interval, and the consistency criterion requires that the peak-to-peak variation of the local activation time (LAT) not exceed a predefined limit.

4. The medical apparatus according to claim 1, the electrophysiological parameter comprising an electrophysiological voltage, and the measure of consistency is indicative of a variation of the electrophysiological voltage.

5. The medical apparatus according to claim 4, the measure of consistency comprising a peak-to-peak variation of the electrophysiological voltage in any given time interval, and the consistency criterion requires that the peak-to-peak variation of the electrophysiological voltage not exceed a predefined limit.

6. The medical apparatus according to claim 1, the 3D map being rendered in a background color, and the visual indication comprising other colors superimposed on the background color at the respective locations to indicate a value of the extracted electrophysiological parameter.

7. A method for electrophysiological mapping, the method comprising:
   acquiring in a sequence of time intervals respective electrophysiological signals from a group of electrodes on a probe while the electrodes contact an area of tissue within a body of a patient;
   acquiring position coordinates of the group of electrodes;
   extracting respective electrophysiological parameters from the respective electrophysiological signals acquired in each time interval in the sequence by each of the electrodes in the group;
   computing for each time interval a respective measure of consistency among the respective electrophysiological parameters extracted from the electrophysiological signals acquired by the electrodes in the group during the time interval, the respective measure of consistency comprising a variation electrophysiological parameter value; and
   displaying a three-dimensional (3D) map of the tissue while superimposing on the map, responsively to the position coordinates, a visual indication of the extracted electrophysiological parameters at the respective locations in the time intervals for which the variation electrophysiological parameter value is within a a predefined consistency criterion range, and automatically discarding from the map the electrophysiological parameters extracted in the time intervals for which the variation electrophysiological parameter value is outside the predefined consistency criterion range.

8. The method according to claim 7, extracting electrophysiological parameters comprising extracting a local activation time (LAT) in a heart of the patient, and computing the measure of consistency comprises computing a measure indicative of a variation of the local activation time (LAT).

9. The method according to claim 8, computing the measure comprising computing a peak-to-peak variation of the local activation time (LAT) in any given time interval, and the consistency criterion requiring that the peak-to-peak variation of the local activation time (LAT) during that time interval not exceed a predefined limit.

10. The method according to claim 7, extracting electrophysiological parameters comprising extracting an electrophysiological voltage in a heart of the patient, and computing the respective measure of consistency comprises computing a measure indicative of a variation of the electrophysiological voltage.

11. The method according to claim 10, computing the measure comprising computing a peak-to-peak variation of the electrophysiological voltage in any given time interval, and the consistency criterion requiring that the peak-to-peak variation of the electrophysiological voltage during that time interval not exceed a predefined limit.

12. The method according to claim 7, displaying the 3D map comprising rendering the 3D map in a background color, and superimposing the visual indication comprising superimposing other colors on the background color at the respective locations indicating respective values of the extracted electrophysiological parameters.

13. A medical apparatus, comprising:
   a probe configured for insertion into a body of a patient and comprising a plurality of electrodes configured to contact tissue within the body in a sequence of time intervals;
   a display screen;
   a position-tracking system configured to acquire position coordinates of the electrodes within the body; and
   a processor configured to:
      acquire a respective electrophysiological signal from a group of the electrodes in each time interval in the sequence while the electrodes contact an area of the tissue at respective locations within the area,
      extract respective electrophysiological parameters from the respective electrophysiological signals acquired in each time interval by the electrodes in the group,
      for each time interval, compute a respective measure of consistency range among the respective electrophysiological parameters extracted from the electrophysiological signals acquired by the electrodes in the group during the time interval, and
      render to the display screen a three-dimensional (3D) map of the tissue while superimposing on the map, responsively to the position coordinates, a visual indication of the extracted electrophysiological parameters at the respective locations of the electrodes in the time intervals for which the respective measure of consistency range is within a predefined consistency criterion boundary, and automatically discarding from the map the electrophysiological parameters extracted in the time intervals for which the respective measure of consistency range is out of satisfy the predefined consistency criterion boundary.

14. The medical apparatus of claim 13, the probe comprising a catheter.

15. The medical apparatus of claim 14, the catheter further comprising a basket catheter.

16. The medical apparatus of claim 13, the position-tracking system comprising a first sensor.

17. The medical apparatus of claim 16, the first sensor comprising a triple-axis sensor.

18. The medical apparatus of claim 17, the position-tracking system comprising a second sensor.

19. The medical apparatus of claim 18, the second sensor comprising a triple-axis sensor.

20. The medical apparatus of claim 18, the second sensor comprising a single-axis sensor.

* * * * *